United States Patent [19]

Colina

[11] Patent Number: 5,039,668

[45] Date of Patent: Aug. 13, 1991

[54] PHARMACEUTICAL COMPOSITIONS CONTAINING LIQUID BEE HONEY

[76] Inventor: Alberto O. Colina, Avenida Country Club No. 96, Colonia Country Club, Mexico City 04220, Mexico

[21] Appl. No.: 349,668

[22] Filed: May 10, 1989

Related U.S. Application Data

[63] Continuation-in-part of Ser. No. 159,604, Mar. 4, 1988, abandoned.

[51] Int. Cl.$^5$ .................. A61K 31/70; A61K 31/51; A61K 31/525; A61K 31/44; A23L 1/30
[52] U.S. Cl. ........................................ 514/52; 514/251; 514/276; 514/345; 514/356; 514/904; 426/72
[58] Field of Search ................. 514/52, 276, 251, 356, 514/345, 904; 426/72

[56] References Cited

U.S. PATENT DOCUMENTS 3,780,185  12/1973  Fields ................................. 426/72
4,220,666  9/1980  Fields ................................. 426/62

Primary Examiner—Alan L. Rotman

[57] ABSTRACT

Therapeutic formulations containing liquid bee honey for the treatment of vitamin deficiency and as a cough supressant. The disclosure is also directed to a preferred embodiment for the formulation of therapeutic formulations containing liquid bee honey.

3 Claims, No Drawings

PHARMACEUTICAL COMPOSITIONS CONTAINING LIQUID BEE HONEY

RELATED APPLICATION

This application is a continuation-in-part of application Ser. No. 07/159,604, filed Mar. 4, 1988.

BACKGROUND OF THE INVENTION

The field of the invention relates to pharmaceutical compositions containing a therapeutic agent in combination with liquid bee's honey, and more particularly, to pharmaceutical compositions useful for the treatment of human illnesses including blood iron deficiencies, bone calcium deficiencies, vitamin deficiencies. In addition, a useful expectorant is also needed for the treatment of certain illnesses.

Liquefied bee's honey is known and various apparatus have been used to prepare bee's honey which includes the heating comb honey at a substantially uniform temperature that is sufficient to liquefy the honey but not too high to melt the wax from the honeycombs. One such useful device is disclosed in U.S. Pat. No. 2,248,867.

Liquiefied bee's honey has been used in the past for the preparation of various food products including, for example, a whipped honey spread, as disclosed in U.S. Pat. No. 4,004,040. Liquid bee's honey appears to have found a very limited use with therapeutic agents. For example, liquid honey has been formulated with active ingredient's for the treatment relief and treatment of internal hemorrhoids and herorrhoidal symptoms wherein said formulation can be taken orally, as disclosed in U.S. Pat. No. 4,761,285.

SUMMARY OF THE PRESENT INVENTION

The compositions of the present invention are directed to therapeutic compositions containing a substantial amount of liquid bee's honey in combination with any one or more active therapeutic ingredients, useful for the treatment of various human illnesses or deficiencies.

DETAILED DESCRIPTION OF THE PRESENT INVENTION

The composition of this invention is a combination of liquid bee's honey and at least one therapeutic or medicinal ingredient.

The liquid bee's honey, useful in the practice of this invention, is preferably prepared by with an apparatus "containing a tank to be treated, by a double boiler, a storage tank connected to a vacuum pump, a process tank, valves to open and closeed each tank and a filter, wild honey is initially poured into tank a and is heated by a double boiler water bath system until liqueficiation is achieved. The temperature must be carefully observed to avoid destruction of the honey and yet not be too high to result in the melting of the wax component of the honey. Once liquefication is achieved, vacuum pump (not shown) connected to storage tank d by connector e, is started and valve b is opened to allow the liquid honey to pass through filter c so that the liquid honey is separated from insects, larvae, organic remains, wax, etc., resulting in the liquid honey being collected in storage tank d. Storage tank is always maintained in a substantially filled condition, during the process, while honey is being transferred to processing tank g through valve e.

Various therapeutic ingredients are incorporated into the liquid honey in the processing tank g. When such ingredients are being added, it is essential that agitator h must be functioning, to insure adequate mixing of the ingredients as well as forcing the honey to the bottom of tank g, thereby minimizing the formation of any air bubbles in the product which, after bottling, could cause the product to degrade.

It is important for the honey to be kept at substantially the same temperature, during the entire process, from the time the honey is initially separated from other components, until individual containers containing the therapeutic products are filled and ready to be delivered to the consumer. Such individual containers are filled by allowing the hot liquid bee's honey to pass through by-pass valve f into a filling pump l which is used to fill individual containers by means of conventional apparatus for this purpose which is well known in the art.

According to the preferred embodiment of this invention, a particularly preferred composition for the administration of vitamin $B_{12}$ is as follows:

| | |
|---|---|
| Vitamin $B_{12}$ (cyanocobalamine) | 50 mcg. |
| Folic acid (sodium salt) | 5 mg. |
| calcium levulinate | 4 gm. |
| histidine hydrochloride | 500 mg. |
| l-lysine hydrochloride | 500 mg. |
| triptophan hydrochloride | 80 mg. |
| liquid bee honey | up to 100 ml. |

The above formulation, containing the ingredients as set forth, to provide a total of 100 ml. of formulation, is administered at the rate of one or two teaspoons per day.

Another preferred formulation for the treatment of vitamin deficiency, is formulated as follows, for each 100 ml. of formulation produced:

| | |
|---|---|
| Vitamin $B_{12}$ (cyanocobalamine) | 50 mcg. |
| Vitamin $B_1$ (thiamine hydrochloride) | 40 mg. |
| Vitamin $B_6$ (pyridoxine hydrochloride) | 40 mg |
| Niacin (nicotinamide) | 300 mg |
| calcium pantothenate | 300 mg. |
| calcium glutamate | 500 mg. |
| histidine hydrochloride | 500 mg. |
| lysine hydrochloride | 60 mg. |
| triptophan hydrochloride | 80 mg. |
| liquid bee honey | balance to 100 ml. |

This preferred multivitamin formulation can be administered orally at the rate of one or two teaspoons per day.

Another embodiment of the present invention relates to a cough formulation in the form of an expectorant or antitusive. This formulation contains the following ingredients, in the amounts specified, for each 100 ml. that is formulated:

| | |
|---|---|
| dextromethorphan hydrobromide | 300 mg. |
| guaifenesin (glycerol guaiacolate) | 800 mg. |
| ammonium chloride | 1 gm. |
| liquid bee honey | balance to 100 ml. |

This formulation is generally administered at the rate of four teaspoons per day.

A further embodiment of the present invention relates to another cough formulation, also in the form of an expectorant or antitusive wherein the formulation contains the following ingredients, in the amounts specified, for each 100 ml. that is formulated:

| | |
|---|---|
| phenylpropanolamine hydrochloride | 400 mg. |
| guaifenesin (glycerol guaiacolate) | 1 gm. |
| flavorant (tulo balsam ticture) | 4 ml. |
| liquid bee honey | balance to 100 ml. |

Another preferred formulation of the present invention, contains the following ingredients, for each 100 ml. that is formulated:

| | |
|---|---|
| Vitamin $B_{12}$ (cyanocobalamine) | 50 mg. |
| sodium folate | 5 mg. |
| niacin (nicotinic acid) | 300 mg. |
| biotin | 3 mg. |
| ferrous gluconate | 400 mg. |
| histidine hydrochloride | 500 mg. |
| l-lysine hydrochloride | 500 mg. |
| triptophan hydrochloride | 80 mg. |
| liquid bee honey | balance to 100 ml. |

What is claimed is:

1. A composition comprising the following ingredients:

| | |
|---|---|
| Vitamin $B_{12}$ | 50 mcg. |
| Folic acid (sodium salt) | 5 mg. |
| calcium levulinate | 4 gm. |
| histidine hydrochloride | 500 mg. |
| l-lysine hydrochloride | 500 mg. |
| triptophan hydrochloride | 80 mg. | an liquid bee honey in an amount sufficient to provide 100 ml. of said composition.

2. A composition comprising the following ingredients:

| | |
|---|---|
| Vitamin $B_{12}$ | 50 mcg. |
| Vitamin $B_1$ | 40 mg. |
| Vitamin $B_6$ | 40 mg. |
| Niacin (nicotinamide) | 300 mg. |
| calcium pantothenate | 300 mg. |
| calcium glutamate | 500 mg. |
| histidine hydrochloride | 500 mg. |
| lysine hydrochloride | 60 mg. |
| triptophan hydrochloride | 80 mg. | and liquid bee honey in an amount sufficient to provide 100 ml. of said composition.

3. A composition comprising the following ingredients:

| | |
|---|---|
| Vitamin $B_{12}$ | 50 mcg. |
| sodium folate | 5 mg. |
| niacin (nicotinic acid) | 300 mg. |
| biotin | 3 mg. |
| ferrous glyconate | 400 mg. |
| histidine hydrochloride | 500 mg. |
| l-lysine hydrochloride | 500 mg. |
| triptophan hydrochloride | 80 mg | and liquid bee honey in an amount sufficient to provide 100 ml. of said composition.

* * * * *